United States Patent
Nobis et al.

(10) Patent No.: US 9,707,029 B2
(45) Date of Patent: Jul. 18, 2017

(54) SHIELD MECHANISMS FOR SURGICAL DEVICES

(71) Applicant: Ethicon LLC, Guaynabo, PR (US)

(72) Inventors: Rudolph H. Nobis, Mason, OH (US); Mark A. Davison, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 174 days.

(21) Appl. No.: 14/135,894

(22) Filed: Dec. 20, 2013

(65) Prior Publication Data

US 2015/0174390 A1    Jun. 25, 2015

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/00083* (2013.01); *A61B 2018/00607* (2013.01); *A61B 2018/1455* (2013.01)

(58) Field of Classification Search
CPC ............ A61B 18/1442; A61B 18/1445; A61B 2018/00083
USPC ...................................... 606/41, 50–52, 207
See application file for complete search history.

(56) References Cited

U.S. PATENT DOCUMENTS

| | | | |
|---|---|---|---|
| 3,841,317 A | 10/1974 | Awais | |
| 5,715,832 A * | 2/1998 | Koblish | A61B 18/1445 600/564 |
| 6,056,735 A * | 5/2000 | Okada | A61B 17/320092 606/1 |
| 2002/0103499 A1 * | 8/2002 | Perez | A61B 5/1411 606/182 |
| 2002/0166946 A1 * | 11/2002 | Iizuka | A61B 1/00087 250/201.2 |
| 2003/0009085 A1 * | 1/2003 | Arai | A61B 18/1492 600/127 |
| 2004/0133195 A1 | 7/2004 | Solomon | |
| 2006/0167450 A1 * | 7/2006 | Johnson | A61B 18/1445 606/48 |
| 2006/0258954 A1 * | 11/2006 | Timberlake | A61B 10/06 600/564 |
| 2007/0198032 A1 * | 8/2007 | Ortiz | A61B 17/076 606/138 |
| 2010/0168773 A1 * | 7/2010 | Funderburk | A61B 17/3213 606/167 |
| 2010/0191052 A1 * | 7/2010 | Surti | A61B 1/00087 600/106 |

(Continued)

*Primary Examiner* — Thomas Giuliani
(74) *Attorney, Agent, or Firm* — Mintz Levin Cohn Ferris Glovsky and Popeo, P.C.

(57) ABSTRACT

Various surgical devices are provided for shielding tissue from potentially harmful byproducts generated by surgical devices that use energy to treat tissue. In general, a shield member is provided that includes a connector element for removably connecting the shield member to a surgical device and a shield body configured to extend adjacent to an energy-emitting end effector of the device. When energy is delivered to treated tissue captured by the end effector, the shield body can be configured to serve as a physical barrier between the end effector and tissue adjacent to the treated tissue. In this way, the shield member can protect the adjacent tissue from potentially harmful byproducts of the end effector, e.g., heat and steam, and/or can deflect the byproducts back toward the treated tissue.

23 Claims, 5 Drawing Sheets

(56) References Cited

U.S. PATENT DOCUMENTS

2014/0135804 A1   5/2014   Weisenburgh, II et al.

* cited by examiner

SHIELD MECHANISMS FOR SURGICAL DEVICES

FIELD

The present invention relates to devices and methods for treating tissue by delivering energy thereto and protecting tissue from collateral damage.

BACKGROUND

Various surgical devices utilize energy to transect and seal tissue. In general, these devices have an end effector on a distal end of a shaft. The end effector often includes opposed jaws configured to grasp tissue therebetween and a cutting mechanism configured to sever the tissue that is positioned between the jaws. The end effector can be coupled to an energy source, for example a radiofrequency (RF) generator, that supplies energy to conductive regions on the opposed jaws, thereby allowing for bipolar delivery of energy to help transect and seal tissue between the opposed jaws.

The use of such energy-based surgical devices can have a number of potentially harmful consequences. For example, heat generated by the flow of energy, e.g., RF energy, between the opposed jaws can raise the temperature of adjacent tissue beyond desirable levels. To help minimize undesirable increases in temperature, some surgical systems flush the surgical site with fluid during surgery. However, this can create steam as the fluid is heated, which can spread to adjacent tissue and/or cloud the surgeon's view. Steam can also be generated by lysis of tissue cells being treated between the opposed jaws.

Accordingly, there remains a need for devices and methods that enhance the safety and efficacy of energy-based surgical devices.

SUMMARY

The present invention generally provides methods and devices for shielding tissue from byproducts of surgical devices. In one aspect, a surgical device is provided that includes a shaft having an end effector extending from a distal end thereof and being configured to treat tissue, at least in part, by delivering energy thereto. The surgical device can also include a shield member having a connector element and a shield body. The connector element can be disposed at a proximal end of the shield member and can be configured to operably couple the shield member to the shaft. The shield body can be configured, in an operative position, to be spaced apart from the end effector. In some embodiments, the surgical device is a cutting device.

The connector element can be configured to connect the shield member to the shaft in a variety of ways. For example, the connector element can attach to the shaft via frictional fit. The connector element can be configured to slide along the shaft when acted upon by a force that exceeds a threshold force. In some embodiments, the connector element can include a locking mechanism that is configured to secure the shield member to one or more positions along the shaft.

The shield body can have a length measured along a longitudinal axis of the shaft that is greater than a length of the end effector, and/or can have a width measured along an axis that is transverse to the longitudinal axis that is greater than a width of the end effector. In some embodiments, the shield body can be parallel to the end effector. In some embodiments, the shield body can extend distally beyond a distal end of the end effector.

In another aspect, a method is provided that includes positioning an end effector of a surgical device adjacent to tissue to be treated by the end effector. The end effector can have a shield member operatively coupled thereto. The method can further include positioning the end effector and the shield member such that at least a portion of the end effector is disposed between the shield member and the tissue to be treated and such that the end effector is disposed between the shield member and a user's line of sight. The method can also include treating the tissue by applying energy thereto from the end effector. The treating can include cutting and coagulating the tissue.

In some embodiments, the positioning of the shield member can include attaching the shield member to a proximal portion of the surgical device and moving the shield member distally until the shield member is disposed adjacent to the end effector. Moving the shield member can include sliding the shield member proximally along a shaft of the surgical device.

BRIEF DESCRIPTION OF DRAWINGS

This invention will be more fully understood from the following detailed description taken in conjunction with the accompanying drawings, in which.

DETAILED DESCRIPTION

Figure 1:
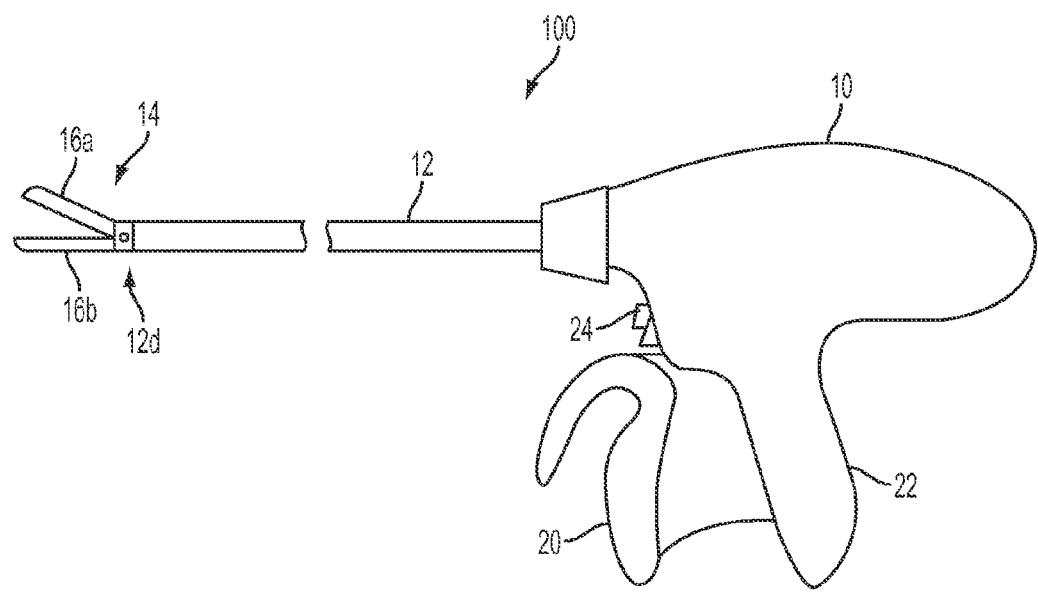
FIG. 1 is a side view of one embodiment of a surgical device that treats tissue using energy.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various surgical devices are provided for shielding tissue from byproducts generated by surgical devices. The surgical devices described herein generally include a handle portion, an elongate shaft, and an effector having opposed jaws configured to engage and treat tissue therebetween using energy. One or more shield members can be configured to attach to one or more locations on the devices to thereby shield tissue adjacent to a treatment site from potentially harmful byproducts generated by the devices, e.g., heat and/or steam. For example, in one embodiment, a shield member is provided that includes a connector element configured to attach the shield member to a surgical device and a shield body extending distally from the connector element. The shield body can be configured to extend adjacent to and spaced apart from an energy-emitting end effector of the device, between the end effector and tissue adjacent to tissue to be treated. In this way, the shield body can help to separate the tissue to be treated from the adjacent tissue, and in some embodiments can be configured to serve as a backdrop to facilitate viewing of the tissue to be treated. Byproducts created by the end effector can be deflected by the shield body back toward the tissue to be treated, thus protecting the adjacent tissue from collateral damage and/or potentially enhancing a treatment effect of the end effector on the tissue to be treated. The connector element can be configured to removably attach the shield member to the surgical device, thereby allowing for the shield member to be repositioned to a desired location along the device and/or removed from the device when not necessary. In some embodiments, the connector element can be slidably connected to the surgical device to allow for axial and rotational movement of the shield member along the device.

A shield member as described herein can be used with a variety of surgical devices that use energy to treat tissue and that can create potentially harmful byproducts. One such electrosurgical device, illustrated in FIG. 1, is configured to grasp and cut tissue using energy. A surgical device 100 can include a proximal handle portion 10, a shaft portion 12, and an end effector 14 for grasping and treating tissue. The proximal handle portion 10 can be any type of pistol-grip or other type of handle known in the art that is configured to carry various actuators, such as actuator levers, triggers or sliders for actuating the end effector 14. In the illustrated embodiment, the proximal handle portion 10 includes a closure grip 20 and a stationary grip 22, and movement of the closure grip 20 toward and away from the stationary grip 22 adjusts a position of the end effector 14. The shaft portion 12 extends distally from the proximal handle portion and can have a bore (not shown) extending therethrough for carrying mechanisms for actuating the jaws. The bore of the shaft portion 12 can carry actuator components for opening the jaws and electrical leads for delivery of electrical energy to electrosurgical components of the end effector 14. The source of the energy can vary, although in an exemplary embodiment the source of the energy is an RF generator (not shown). The RF generator can be of a type known to those skilled in the art. The RF generator, or other energy source, can be located within the handle portion 10, or it can be a remote unit to which the device 100 can connect. In such embodiments, the end effector 14 can be adapted for transecting captured tissue and for sealing the captured tissue margins with controlled application of energy, and the energy can be controlled using a firing trigger, such as firing button 24 shown in FIG. 1, or another suitable actuator.

Figure 2:
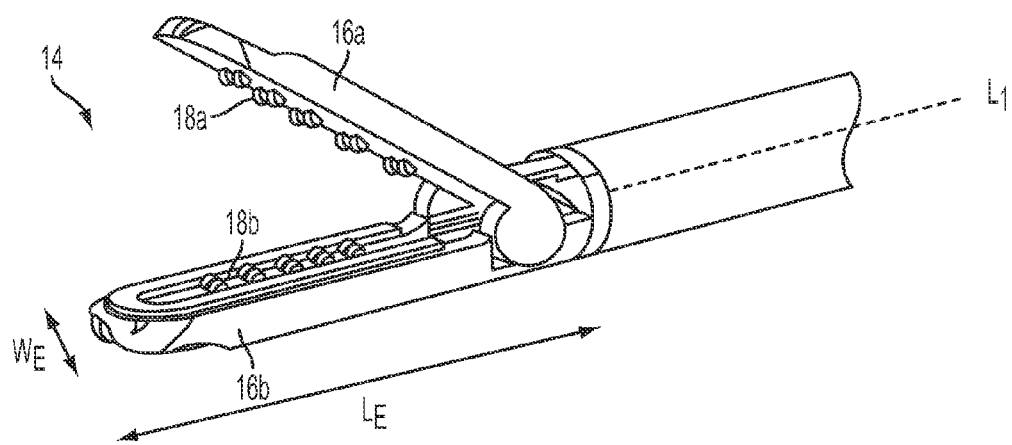
FIG. 2 is a perspective view of an end effector of the surgical device of FIG. 1 in an open position.

The end effector can have a variety of sizes, shapes, and configurations. As shown in FIGS. 1 and 2, the exemplary end effector 14 can include first and second jaws 16a, 16b disposed at a distal end 12d of the shaft portion 12. The jaws 16a, 16b can be adapted to close or approximate about an axis. Each of the jaws 16a, 16b can have gripping elements 18a, 18b formed on inner surfaces thereof to facilitate gripping tissue between the jaws 16a, 16b. Both of the jaws 16a, 16b can be moveable relative to the shaft portion 12 or alternatively a single jaw can rotate so that the end effector 14 can move between a first, open position in which the jaws 16a, 16b are positioned at a distance apart to a second, closed position in which the jaws 16a, 16b are moved toward one another and are substantially opposed. When the jaws 16a, 16b are in the second, closed position, a longitudinal axis of the lower jaw 16a can be substantially parallel to a longitudinal axis of the upper jaw 16b and the upper and lower jaws 16a, 16b can be in direct contact. In the illustrated embodiment, the upper jaw 16a can pivot relative to the shaft portion 12 and relative to the lower jaw 16b while the lower jaw 16b remains stationary. In particular, the upper jaw 16a can pivot toward the lower jaw 16b when the closure grip 20 is moved toward the stationary grip 22.

In the illustrated embodiment, the jaws 16a, 16b have a substantially elongate and straight shape, but a person skilled in the art will appreciate that one or both of the jaws 16a, 16b can be curved. The jaws 16a, 16b can have any suitable axial length $L_E$ for engaging tissue, either same or different from one another, where the axial length $L_E$ is measured along a longitudinal axis $L_1$ of the upper and lower jaws 16a, 16b, as shown in FIG. 2. The jaws 16a, 16b can have any width $W_E$, either same or different from one another, measured along an axis perpendicular to the longitudinal axis $L_1$. The length $L_E$ and the width $W_E$ of the jaws 16a, 16b can be selected based on the targeted anatomical structure for transection and/or sealing.

Figure 3:
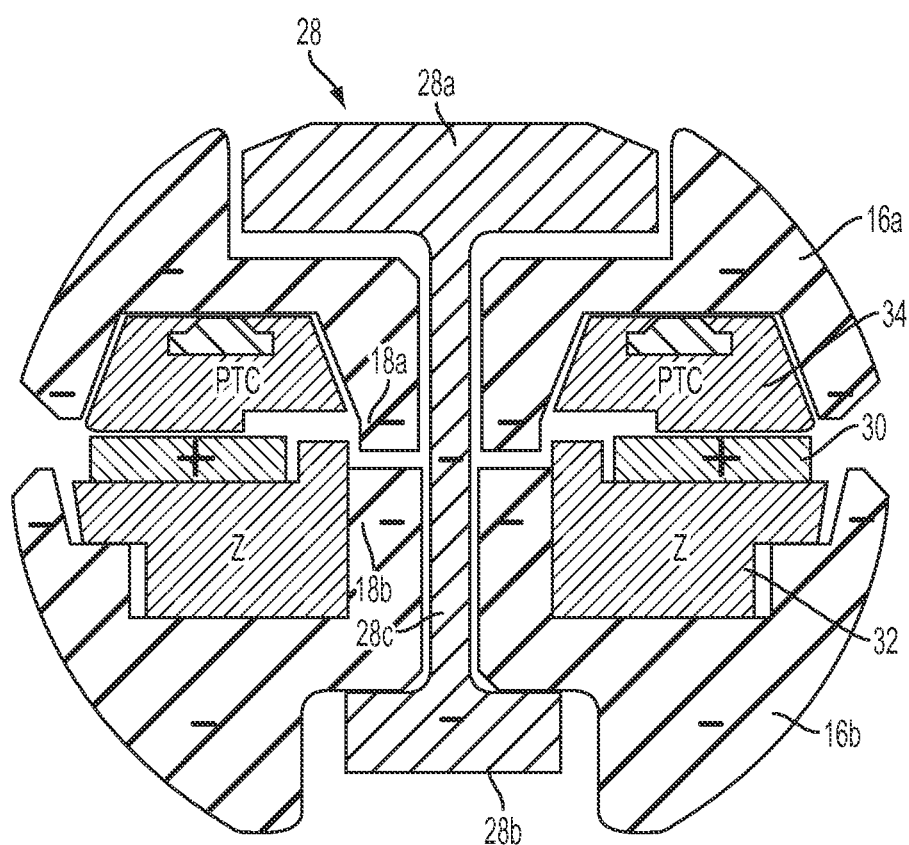
FIG. 3 is a cross-sectional view of the end effector of FIG. 2 in a closed position.

The device 100 can include a cutting member configured to transect tissue captured between the jaws, and the cutting member can have various sizes, shapes, and configurations. The cutting member can have a size and shape configured to transect or cut various thicknesses and types of tissue positioned between the jaws 16a, 16b of the end effector 14. An exemplary cutting member 28 is illustrated in FIG. 3. The cutting member 28 includes upper and lower horizontal clamping components 28a, 28b that are connected by a vertical knife component 28c. The clamping components 28a, 28b can function to clamp the jaws 16a, 16b together while the vertical knife component 28c functions to sever tissue captured between the jaws 16a, 16b. The knife component 28c can have a sharp or serrated edge configured to transect the tissue. The cutting member 28 can be configured to advance distally and retract proximally relative to the jaws 16a, 16n in various ways. For example, the cutting member 28 can be electrically coupled to a motor (not shown) disposed in the handle 10. Activation of the motor can advance and/or retract the cutting member 28 and can optionally include a controller configured to send a control signal to the motor.

The jaws 16a, 16b and/or the cutting member 28 can be configured to contact and deliver energy to tissue disposed between the jaws 16a, 16b. In the exemplary embodiment of FIGS. 1-3, the upper jaw 16a, the lower jaw 16b, and the cutting member 28 can be coupled to a first electrical polarity. In one embodiment, an insert 34, such as one made of a Positive Temperature Coefficient (PTC) material, can be positioned within the upper jaw 16a and can help control the power delivered to the tissue positioned between the jaws 16a, 16b. An electrode 30 can be positioned within the lower jaw 16b, which can be coupled to a different electrical polarity than the lower jaw 16b. To help insulate the lower jaw 16b from the electrode 30, an insulator 32 can be positioned therebetween. In this way, with the upper jaw 16a and the lower jaw 16b at a first polarity and the electrode 30 at a different polarity, the jaws 16a, 16b can operate in a bipolar mode to heat and seal tissue. It will be appreciated by a person skilled in the art that the polarities of each of the components of the end effector 14 can be changed to facilitate delivery of electrical energy. Also, the plus (+) and minus (−) labels of FIG. 3 are used to illustrate exemplary polarities, but a person skilled in the art will appreciate that any of the illustrated polarities (i.e., the (+) and (−) labels) can be reversed.

Figure 4:
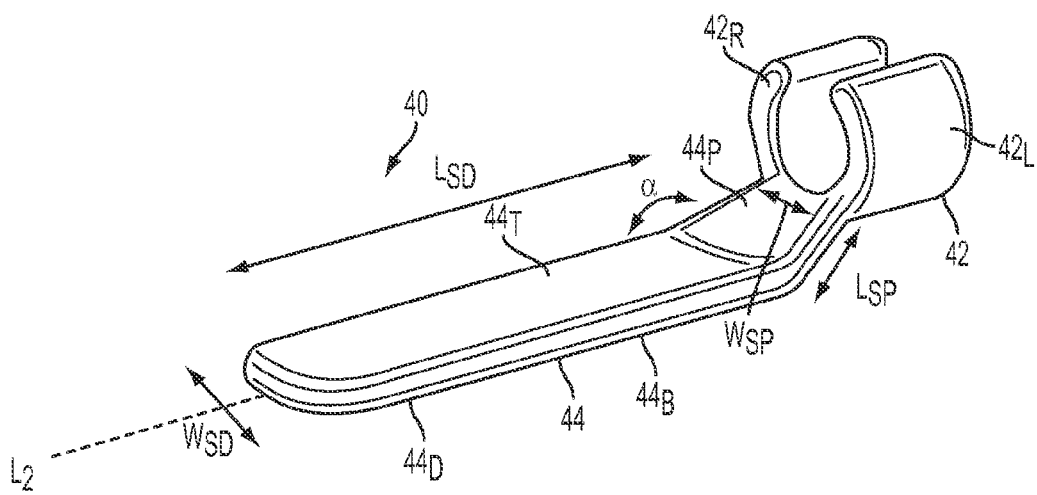
FIG. 4 is a perspective view of one embodiment of a shield member.
Figure 5:
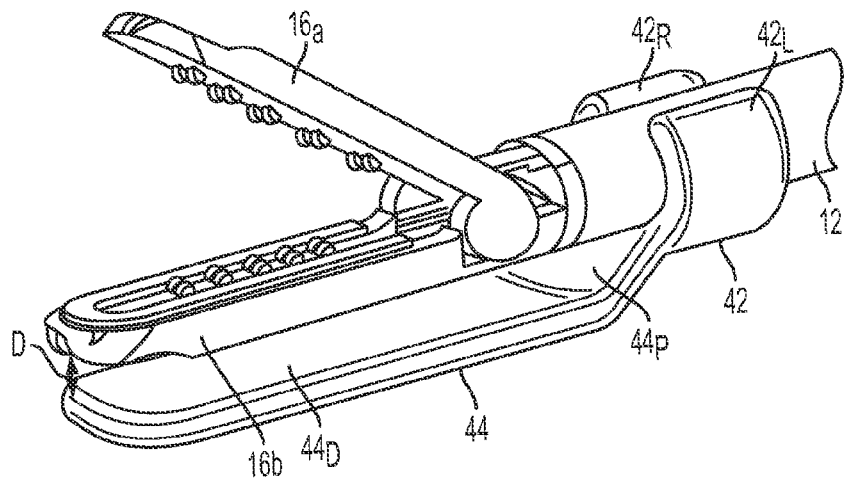
FIG. 5 is a perspective view of the shield member of FIG. 4 attached to a shaft of the surgical device of FIG. 1.

FIGS. 4-5 illustrate an exemplary embodiment of a shield member for protecting tissue adjacent to a treatment site from potentially harmful byproducts of a surgical device, such as the device 100 described above. Although the use of a shield member as described herein is made with reference to the device 100, it will be appreciated by a person skilled in the art that shield members can be used with a variety of surgical devices that apply energy to tissue and that can produce potentially harmful byproducts.

An exemplary shield member can include a shield body that can be configured to extend adjacent to and spaced apart from an energy-emitting end effector of one or more surgical devices. The shield body can have any shape and size that is operative to protect tissue adjacent to a treatment site from byproducts of the one or more devices. By way of non-limiting example, the shield body can be in the shape of a cone, a tube, a plate, etc. A person skilled in the art will appreciate that the dimensions of the shield body can vary depending upon the requirements of a given application. In one embodiment, the shield body is generally parallel to the end effector.

An exemplary embodiment of a shield member 40, illustrated in FIG. 4, has a shield body that is a plate 44. The plate 44 can have a proximal portion $44_P$ and a distal portion $44_D$. The proximal portion $44_P$ can serve to orient the distal portion $44_D$, which is generally the component that performs a shielding function. The distal portion $44_D$ can have any dimensions that render it suitable for its intended purpose. In the illustrated embodiment, the distal portion $44_D$ is substantially planar and rectangular in shape, and defines a longitudinal axis $L_2$ along a length $L_{SD}$ thereof. The length $L_{SD}$ of the distal portion can be less than, equal to or greater than a length of an end effector to which the shield member 40 is attached. Generally, however, the length $L_{SD}$ is at least equal to the length of the end effector. Similarly, a width $W_{SD}$ of the distal portion $44_D$ can be less than, equal to, or greater than a width of the end effector, although generally the width $W_{SD}$ is at least equal to the width of the end effector. The proximal portion $44_P$ can also be substantially planar and can extend at an angle α to the distal portion $44_D$. The proximal portion $44_P$ can connect the distal portion $44_D$ to the connector element and can have any suitable length $L_{SP}$ and width $W_{SP}$, which can be either constant or varying along the length $L_{SP}$ thereof.

The plate 44 can be sized in accordance with various other factors, including, e.g., a type and/or a volume of tissue present at a surgical site, an expected amount of byproducts generated by the end effector, an amount of clearance needed around the treatment site, etc. In some embodiments, the angle α and each of the lengths $L_{SP}$, $L_{SD}$, and/or the widths $W_{SP}$, $W_{SD}$ of the plate 44 can be sized to allow for the plate 44 to pass through a small surgical incision and/or a cannulated body to a surgical site. For the illustrated embodiment, the length $L_{SD}$ can generally be in a range of about 10 to 50 mm, the width $W_{SD}$ can be in a range of about 3 to 12 mm, the length $L_{SP}$ can be in a range of about 0.1 to 3 mm, the width $W_{SP}$ can be in a range of about 2 to 12 mm, and the angle α can be in a range of about 0 to 90 degrees. In general, a shield body as described herein can have a length in a range of about 10 to 55 mm and a width in a range of about 3 to 12 mm. The thickness of the shield body can vary to allow the shield body to be rigid or semi-rigid.

The plate 44 can have one or more features thereon to facilitate deflection of potentially harmful byproducts from adjacent tissue and/or the pushing away of adjacent tissue. For example, in the illustrated embodiment, the plate 44 can have a radius of curvature across widths $W_{SP}$, $W_{SD}$ thereof, such that a bottom surface $44_B$ of the plate 44 is convex and a top surface $44_T$ is concave. The convex bottom surface $44_B$ can help to push tissue beneath the plate 44 away from a treatment site. The concave top surface can $44_T$ can help to deflect potentially harmful byproducts of the end effector away from tissue that is beneath and to left and right sides of the plate 44, and can also help to deflect the byproducts back towards treated tissue captured by the end effector. For example, the concave top surface $44_T$ can deflect heat and/or steam generated by the end effector away from adjacent tissue that is disposed below the bottom surface $44_B$, and back toward tissue captured by the end effector. In some embodiments, a shield body can extend around any circumference of an end effector, for example the shield member can extend around about half a circumference of the end effector. In this way, the shield body can help to deflect potentially harmful byproducts of the end effector away from adjacent tissue disposed on multiple sides of the end effector.

To help avoid injuring tissue as the shield member 40 advances into a surgical site, one or more edges of the plate 44 can be configured to be atraumatic. For example, as shown in FIG. 4, every corner of the plate 44 is chamfered such that the plate 44 does not have any sharp edges. In particular, edges connecting side surfaces of the plate 44 to the top and bottom surfaces $44_T$, $44_B$, can all be chamfered.

In some embodiments, the plate 44 can be configured to function as a backdrop to facilitate viewing of a surgical site, either directly by a surgeon or endoscopically using, e.g., a camera. By way of non-limiting example, the plate 44 can have a color, e.g., white, which can provide a sharp contrast with a color of tissue at the surgical site. Additionally or alternatively, plate 44 can have dimensions that are larger than corresponding dimensions of an end effector to which the plate 44 is attached, such that the plate 44 can serve as a backdrop to tissue captured within the end effector and/or tissue to be treated by the end effector.

A connector element can be disposed on the shield body for attaching the shield body to one or more surgical devices. The connector element can be any feature that effects attachment of the shield body to the one or more surgical devices, for example a ring that can slide over the surgical device, a latch that can connect to a mating element of the surgical device, a magnet, a belt, an adhesive, etc. The connector element is preferably disposed along a proximal portion of the shield body such that it can attach to shaft portion of the device that is proximal to an end effector of the device, although it will appreciated by a person skilled in the art that the connector element can be disposed on any portion of the shield body and can be configured to attach to any portion of the one or more devices. In the illustrated embodiment, the connector element is a snap ring 42 disposed on a proximal end of the plate 44 and configured to removably attach the shield member 40 to a surgical device, thus allowing for removal of the shield member 40 from the device when not necessary or desired.

The snap ring 42 can have opposed arms, such as right and left arms $42_R$, $42_L$, which can be configured to "snap" onto a substantially cylindrical portion of a surgical device, e.g., a shaft. The right and left arms $42_R$, $42_L$ can be made from a material that is sufficiently flexible to allow the arms $42_R$, $42_L$ to couple to a surgical device. In this way, the arms $42_R$, $42_L$ can be forced into an expanded configuration as the shield member 40 is coupled onto the shaft, and can "snap" back towards a resting configuration when the shaft is fully disposed between the arms $42_R$, $42_L$. The snap ring 42 can be securely attached to the shaft, e.g., via friction fit, interference fit, etc., to help reduce a risk of accidental removal or movement of the shield member 40 along the shaft. For example, an inner diameter of the snap ring 42 in the resting configuration can be smaller than a corresponding outer diameter of a portion of the shaft. In some embodiments, an inner surface of the snap ring 42 can have one or more features thereon for frictionally engaging the shaft, e.g., grips, ribs, etc.

The shield member can be configured generally for use with a variety of different surgical devices, or it can be specially customized for use with a particular surgical device. As shown in FIG. 5, the shield member 40 can be configured for use with the surgical device 100. In particular, the snap ring 42 can have an inner diameter that corresponds to an outer diameter of the shaft 12 when the snap ring 42 is in the resting configuration. The plate 44 can be configured to extend adjacent to the lower jaw 16b, and can have a size and a shape that corresponds to a size and a shape of the jaws 16a. 16b and/or of an access instrument, e.g., a cannula, through which the plate 44 is inserted into a patient's body. In particular, the radius of curvature of the plate 44 can correspond to a radius of curvature of a bottom surface of the lower jaw 16b. The length $L_{SD}$ and the width $W_{SD}$ of the distal portion $44_D$ of the plate 44 can each be slightly larger than the length L and the width $W_E$ of the jaws 16a, 16b, respectively, which can help to deflect byproducts that are projected radially outward from the jaws 16a, 16b. Also, the shield member 40 can be configured such that the plate 44 extends distally beyond a distal end of the jaws 16a, 16b when the snap ring 42 is attached to a distal portion of the shaft 12.

As shown in FIG. 5, the distal portion $44_D$ of the plate 44 can be configured to be spaced apart from the lower jaw 16b by a distance D, such that the plate 44 does not contact the end effector 14 along any portion thereof. The distance D can be constant or varying along a length of the distal portion $44_L$. In the illustrated embodiment, the longitudinal axis $L_2$ of the shield member 40 is configured to be substantially parallel to the longitudinal axis $L_1$ of the end effector 14, such that the distance D between the distal portion $44_D$ and the end effector 14 is substantially constant along the length $L_{SD}$ of the distal portion $44_D$ when the shield member 40 is attached to the shaft 12. The distance D can depend upon the angle α between the proximal and distal portions $44_P$, $44_D$, of the plate 44, as well as the length $L_{SP}$ of the proximal portion $44_P$. For example, where the angle α is small, the distance D between the shield member 40 and the end effector can be large, and where the angle α is large, the distance D between the shield member 40 and the end effector can be small. It will be appreciated by a person skilled in the art that the proximal and distal portions $44_P$, $44_D$ can be configured to allow for the angle α to vary. This can allow a surgeon to alter the distance D between the shield member 40 and the end effector, for example in accordance with a size of the end effector, an anatomy of the surgical site, and/or an amount of steam emitted by the end effector. In such embodiments, the proximal portion $44_P$ can be connected to the distal portion $44_D$ by, e.g., a hinge or a bendable material.

Where one or more components of the end effector are movable relative to the shaft, the shield member can be configured to move along with the movable component of the end effector. In one embodiment, a shield member configured to move along with the movable component can be attached to the movable component by a connector element, for example by a connector element disposed on a distal portion of the shield member. In an alternative embodiment, a shield member can have a connector element that is attached to a stationary portion of the surgical device and a shield body that is movably attached to the connector element and configured to move along with the moveable component. By way of non-limiting example, a shield member configured to extend adjacent to the upper jaw 16a can have a shield body that is operatively connected to the closure grip 20, such that actuation of the closure grip 20 causes simultaneous movement of the upper jaw 16a and the shield body.

In some embodiments, the connector element can be configured to slide axially and/or to rotate relative to the surgical device. For example, the snap ring 42 can be configured to remain at one position on the shaft 12, e.g., by interference fit, friction fit, etc., unless acted on by a force that exceeds a threshold force. In this way, a surgeon can selectively rotate and/or slide the shield member 40 by applying a force thereto that exceeds a threshold force. By rotating the shield member 40, the surgeon can position the plate 44 such that it can protect adjacent tissue located on different sides of the end effector 14. By sliding the shield member 40 along the shaft 12, the surgeon can move the shield member 40 between an operative position, shown in FIG. 5, in which the shield member 40 is positioned adjacent to the end effector 14, and a retracted position in which the shield member 40 is positioned out of the way of the end effector 14. In the illustrated embodiment, the shield member 40 can rotate by more than 180 degrees to protect tissue on multiple sides of the end effector 14 and can slide along an entire length of the shaft 12, although the movement of the shield member 40 can be limited to a predetermined range of angular and axial movement.

In other embodiments, the shield member can be prevented from sliding and/or rotating along the surgical device once the shield member is attached thereto. By way of non-limiting example, a fit between the connector element and the shaft can be too tight to allow for any motion of the shield member with respect to the shaft once attached thereto. In another embodiment, the shield member can be prevented from rotating by one or more rails extending longitudinally along the shaft 12. One or more detents disposed on an inner surface of the snap ring 42 can be configured to slide along the one or more rails when the shield member is connected to the shaft 12. The rails can thus prohibit the snap ring 42 from rotating relative to the shaft 12, but can allow for sliding of the snap ring 42 relative to the shaft 12. Conversely, the one or more rails can extend in a circumferential direction around the shaft 12 to allow for the snap ring 42 to rotate relative to the shaft 12 while preventing axial sliding of the snap ring 42 relative to the shaft 12. A person of skill in the art will appreciate that the one or more rails can have a length configured to limit angular and/or axial movement of the shield member to a confined range.

In some embodiments, a connector element can have a locking mechanism thereon which can be configured to fixedly secure a shield member to a surgical device. The locking mechanism can be any feature that allows for selective securing and removal of the shield member to and from the surgical device. For example, the locking mechanism can be a set screw that can be screwed into the connector element to lock the connector element to the surgical device and unscrewed to release the connector element from the surgical device. In some embodiments, the locking mechanism can be activated by an actuation member, e.g., a switch, a latch, a button, etc., which can move the shield member between a locked position in which the shield member is fixed in one position, and an unlocked position in which the shield member can move relative to the surgical device. The surgical device can have one or more engagement features thereon to help lock the shield member in one or more positions thereon, for example a shaft of the surgical device can have one or more bores for receiving a set screw passing through the connector element. However, engagement features of the surgical device for mating with the shield member can be located anywhere on the surgical device.

Figure 6:
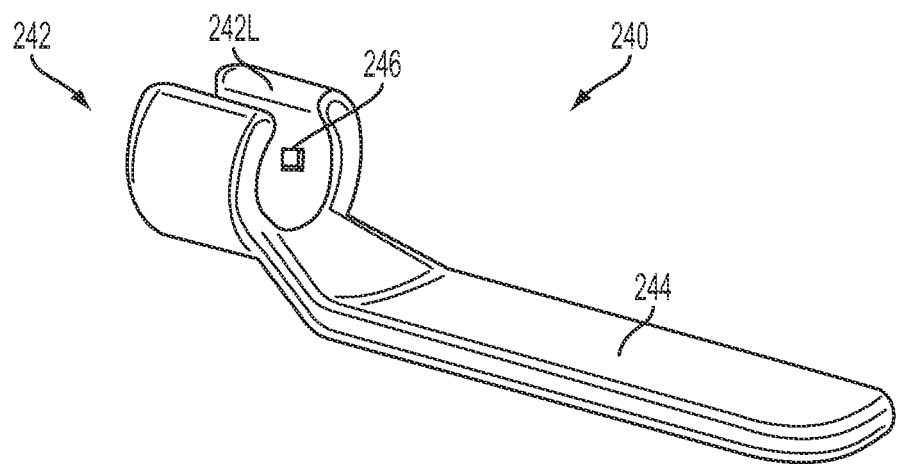
FIG. 6 is a perspective view of another embodiment of a shield member.
Figure 7:
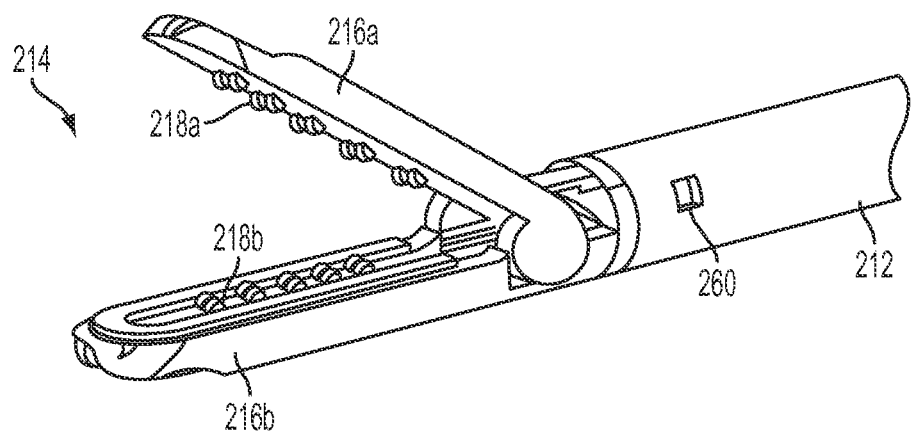
FIG. 7 is a perspective view of another embodiment of an end effector that treats tissue using energy.

Referring now to FIG. 6, another embodiment of a shield member 240 has a snap ring 242 with a locking mechanism thereon for securing the shield member 240 to a surgical device. In particular, the locking mechanism can include a detent 246 disposed on an inner surface 242i of the snap ring 242. The detent 246 can be any shape and size, and can be located on any portion of the inner surface 242i. In the illustrated embodiment, the detent 246 can be configured to mate with a corresponding recess 260 on a shaft 212, as shown in FIG. 7, of a surgical device to thereby lock the shield member 240 to the shaft 212. The detent 246 can be made from one or more materials that are sufficiently flexible to allow the snap ring 242 to slide onto and off of the shaft 212. In some embodiments, the detent 246 can be configured to be compressed, e.g., like a button, upon the application of force thereto, such that the detent 246 is compressed as the detent 246 slides over a surface of the shaft 212, and "pops" back out once the detent 246 is positioned over the recess 260. It will be appreciated by a person skilled in the art that there can be one or more detents on a connector element and one or more recesses on a shaft, which can allow a shield member to be locked in various positions along the shaft. For example, a first recess can be located on a distal portion of the shaft 212 and can be used to lock the shield member 240 in an operative position, and a second recess can be located on a proximal portion of the shaft 212 to lock the shield member 240 in a retracted position. It will also be appreciated by a person skilled in the art that positions of the detent and the recess can be reversed, e.g., the recess can be on the connector element and the detent can be on the shaft.

To facilitate insertion of a shield member into a patient's body, e.g., through a cannula, one or more portions of the shield member can be configured to move between a collapsed configuration and an expanded configuration. By way of non-limiting example, one or more components of the shield member can be connected to one another by hinges that allow for the one or more components to pivot between a collapsed configuration in which the components are substantially flush against a surface of the surgical device and an expanded configuration in which at least the shield body is spaced apart from the surgical device. In some embodiments, one or more portions of a shield member can be formed from a shape memory material, which can include a single material or any combination of materials, such that at least a shield body of the shield member is biased away from an energy-emitting end effector to which the shield member is attached. Non-limiting examples of shape memory materials include copper-zinc-aluminum-nickel alloys, copper-aluminum-nickel alloys, nickel-titanium alloys such as Nitinol, thermoplastic materials such as Nylon or Nylon blends, and shape memory polymers such as Veriflex™. The shape memory material can facilitate the shield body being biased to an expanded configuration in which the shield body is spaced apart from the end effector, as discussed above. The shape memory material can facilitate advancement of the shield member into tissue by allowing any or all portions of the shield body to be deformed or bent in a collapsed in which the shield body has a smaller width than a width thereof in an expanded configuration, while also allowing the shield body to automatically move from the collapsed configuration to the expanded configuration.

The shield members disclosed herein can be made from any one or more materials that are capable of withstanding high temperatures and/or high levels of moisture that can be produced by surgical devices. In some embodiments, the connector element can be made from one or more different materials than the shield body. By way of non-limiting example, the connector element can be made from any suitable metal such as stainless steel or any suitable thermoplastic, e.g., polycarbonate, nylon, polyethylene, etc. The shield body can be made from any suitable thermal insulating and/or non-conductive thermoplastic, e.g., polycarbonate, nylon, polyethylene, etc.

The surgical devices disclosed herein can be generally used to grasp, cut, and seal tissue by applying energy thereto. In an exemplary embodiment, a surgical device is used to cut and seal tissue using RF energy. The device 100 and the shield member 40 can be used, for example, in the exemplary surgical procedure for transecting and sealing tissue illustrated in FIG. 8. Although this procedure is explained using the device 100 and the shield member 40, other surgical devices and shield members disclosed herein can be used.

Figure 8:
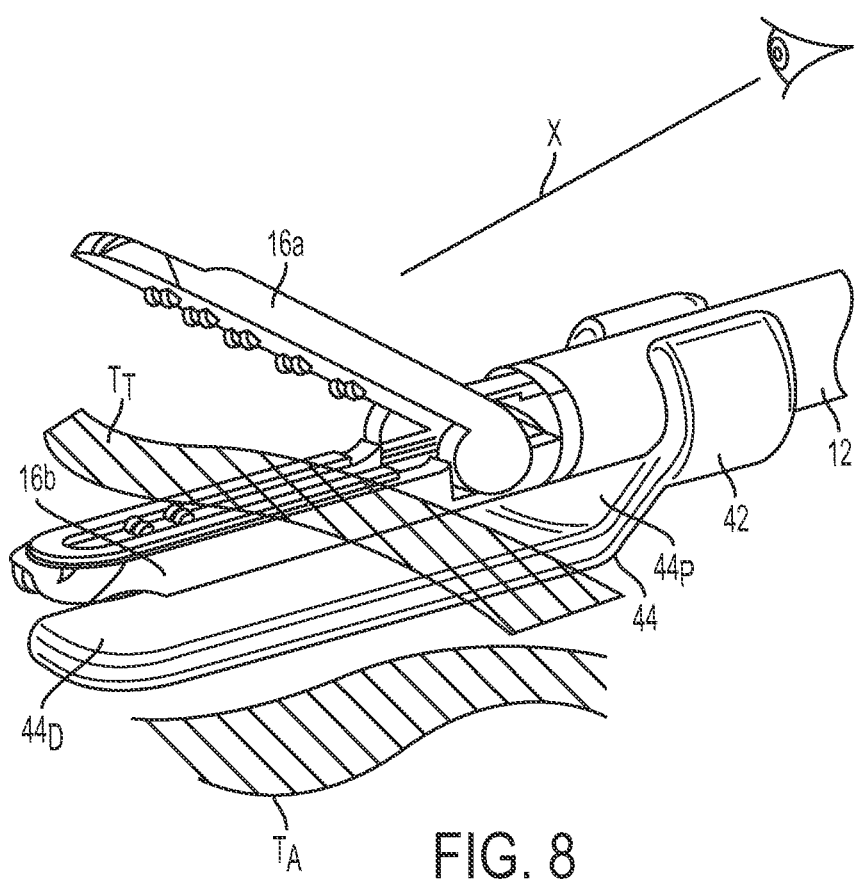
FIG. 8 is a perspective view of the surgical device of FIG. 1 being used to treat tissue and having the shield member of FIG. 4 attached thereto.

In use, the shield member 40 can be attached to the device 100 by inserting the snap ring 42 over the shaft 12. In some embodiments, the shield member 40 can be attached to the shaft 12 along a proximal portion thereof and then, before energy is applied to tissue to be treated, the shield member 40 can be slid proximally until the plate 44 is in the operative position. In this way, the shield member 40 can be kept out of the way until byproducts created by the end effector 14 are produced. In other embodiments, the shield member 40 can be initially attached to the shaft 12 in the operative position. At least a distal portion of the device 100 can be inserted into a body of a patient in accord with customary surgical procedures, which can include open surgery or minimally invasive surgery, e.g., using a cannula. The end effector 14 can be positioned such that tissue to be treated $T_T$ is captured between the jaws 16a, 16b, as shown in FIG. 8, and such that the end effector 14 is disposed between the shield member 40 and a user's line of sight X. In this way, the plate 44 can serve as a backdrop to help the user view the tissue to be treated $T_T$. As mentioned above, a color of the plate 44 can be optimized to provide this backdropped view. Where the shield member 40 has been attached to the distal end of the shaft 12 before insertion of the end effector 14 into the patient's body, the plate 44 can also help to move adjacent tissue $T_A$ and keep the adjacent tissue $T_A$ away from the tissue to be treated $T_T$. The closure grip 22 can then be manipulated to move toward the stationary grip 20 to pivot the upper jaw 16a toward the lower jaw 16b. When the tissue $T_T$ is engaged between the jaws 16a, 16b, depressing the firing trigger 24 can activate various elements in the device 100 to cause the cutting member 28 to advance toward the end effector 14 and/or cause energy to be delivered to the jaws 16a 16b. Energy delivery to the various conductive components of the jaws 16a, 16b can cause current flow through the tissue to be treated $T_T$ as described above, and can produce potentially harmful byproducts, e.g., steam and/or heat. The plate 44, which is positioned adjacent to the end effector 14, can thus serve as a physical barrier to prevent the spread of steam and/or heat to the adjacent tissue $T_A$, which is disposed below the bottom surface $44_B$ of the plate 44. In particular, the plate 44 can deflect steam and/or heat away from the adjacent tissue $T_A$ and back toward the tissue $T_T$ captured between the jaws 16a, 16b.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a shaft having an end effector in contact with a distal end thereof, the end effector being configured to treat tissue, at least in part, by delivering energy thereto when the end effector is in contact with the distal end of the shaft, the end effector further comprising a cutting member configured to advance distally with respect to the end effector to transect tissue treated by the end effector; and
   an atraumatic shield member such that the shield member is not configured to cut tissue, the atraumatic shield member having a connector element at a proximal end thereof that is configured to detachably couple the shield member to the shaft and a shield body extending distally from the connector element, the shield body being configured, in an operative position, to be spaced apart from the end effector.

2. The surgical device of claim 1, wherein the connector element attaches to the shaft via frictional fit.

3. The surgical device of claim 1, wherein the connector element is configured to slide along the shaft when acted upon by a force that exceeds a threshold force.

4. The surgical device of claim 1, wherein the connector element includes a locking mechanism configured to secure the shield member to one or more positions along the shaft.

5. The surgical device of claim 1, wherein the shield body is parallel to the end effector.

6. The surgical device of claim 1, wherein the shield body extends distally beyond a distal end of the end effector.

7. The surgical device of claim 1, wherein a length of the shield body measured along a longitudinal axis of the shaft is equal to or greater than a length of the end effector.

8. The surgical device of claim 1, wherein a width of the shield body measured along an axis that is transverse to a longitudinal axis of the shaft is equal to or greater than a width of the end effector.

9. The surgical device of claim 1, wherein the surgical device treats tissue using electrical energy.

10. The surgical device of claim 1, wherein the end effector comprises a first jaw pivotally coupled to a second jaw and the second jaw is stationary with respect to the shaft.

11. A surgical device, comprising:
    a shaft having an end effector in contact with a distal end thereof, the end effector having a first jaw pivotally coupled to a second jaw and being configured to treat tissue, at least in part, by delivering energy thereto when the end effector is in contact with the distal end of the shaft, the end effector further comprising a cutting member configured to advance distally with respect to the end effector to transect tissue disposed between the first jaw and the second jaw; and
    a shield member having a connector element at a proximal end thereof that is configured to operably couple the shield member to the shaft and a shield body extending distally from the connector element, the shield body being configured, in an operative position, to be spaced apart from the end effector,
    wherein a width of the shield body measured along an axis that is transverse to a longitudinal axis of the shaft is equal to or greater than a diameter of the shaft.

12. The surgical device of claim 11, wherein the connector element attaches to the shaft via frictional fit.

13. The surgical device of claim 11, wherein the connector element is configured to slide along the shaft when acted upon by a force that exceeds a threshold force.

14. The surgical device of claim 11, wherein the connector element includes a locking mechanism configured to secure the shield member to one or more positions along the shaft.

15. The surgical device of claim 11, wherein the shield body is parallel to the second jaw, the second jaw being a stationary jaw.

16. The surgical device of claim 11, wherein the second jaw is stationary with respect to the shaft.

17. A surgical device, comprising:
    a shaft having an end effector extending from a distal end thereof, the end effector having a first jaw pivotally coupled to a second jaw and being configured to treat tissue, at least in part, by delivering energy thereto;
    a cutting member configured to advance distally with respect to the end effector to transect tissue captured between the first and second jaw, wherein the cutting member is configured to engage at least one of the first and second jaws to clamp the first and second jaws together as the cutting member advances distally with respect to the end effector; and a shield member having a connector element at a proximal end thereof that is configured to operably couple the shield member to the shaft and a shield body extending distally from the connector element, the shield body being positioned below the shaft when viewed with a line of sight perpendicular to a longitudinal plane extending through the shaft and configured, in an operative position, to be spaced apart from the end effector.

18. The surgical device of claim 17, wherein the connector element attaches to the shaft via frictional fit.

19. The surgical device of claim 17, wherein the connector element is configured to slide along the shaft when acted upon by a force that exceeds a threshold force.

20. The surgical device of claim 17, wherein the connector element includes a locking mechanism configured to secure the shield member to one or more positions along the shaft.

21. The surgical device of claim 17, wherein the shield body is parallel to the second jaw, the second jaw being a stationary jaw.

22. The surgical device of claim 17, wherein a width of the shield body measured along an axis that is transverse to a longitudinal axis of the shaft is equal to or greater than a width of the end effector.

23. The surgical device of claim 17, wherein the second jaw is stationary with respect to the shaft.

* * * * *